(12) United States Patent
Sample

(10) Patent No.: US 7,641,667 B2
(45) Date of Patent: Jan. 5, 2010

(54) TISSUE CUTTING INSTRUMENT

(75) Inventor: Philip B. Sample, Arlington, MA (US)

(73) Assignee: Smith & Nephew, Inc., Memphis, TN (US)

( * ) Notice: Subject to any disclaimer, the term of this patent is extended or adjusted under 35 U.S.C. 154(b) by 638 days.

(21) Appl. No.: 10/058,122

(22) Filed: Jan. 29, 2002

(65) Prior Publication Data
US 2003/0144681 A1  Jul. 31, 2003

(51) Int. Cl.
A61B 17/32 (2006.01)

(52) U.S. Cl. .................. 606/167; 408/213; 407/33; 407/53; 407/112

(58) Field of Classification Search .................. 606/79, 606/80, 159, 166, 167, 170, 180, 171, 127, 606/128, 174; 604/22; 407/53, 33, 112; 30/272.1, 278; 408/213
See application file for complete search history.

(56) References Cited

U.S. PATENT DOCUMENTS

| | | | |
|---|---|---|---|
| 4,203,444 A | | 5/1980 | Bonnell et al. |
| 4,274,414 A | | 6/1981 | Johnson et al. |
| 4,598,710 A | * | 7/1986 | Kleinberg et al. ........... 606/170 |
| 4,788,976 A | * | 12/1988 | Dee ............................. 606/167 |
| 5,123,904 A | | 6/1992 | Shimomura et al. |
| 5,254,130 A | * | 10/1993 | Poncet et al. ............... 606/206 |
| 5,269,785 A | | 12/1993 | Bonutti |
| 5,275,608 A | * | 1/1994 | Forman et al. .............. 606/170 |
| 5,437,630 A | * | 8/1995 | Daniel et al. ................. 604/22 |
| 5,490,860 A | * | 2/1996 | Middle et al. ............... 606/171 |
| 5,549,637 A | * | 8/1996 | Crainich ..................... 606/207 |
| 5,630,826 A | * | 5/1997 | Sastri .......................... 606/170 |
| 5,632,746 A | * | 5/1997 | Middleman et al. ........... 606/78 |
| 5,649,955 A | * | 7/1997 | Hashimoto et al. ......... 606/205 |
| 5,662,670 A | * | 9/1997 | Michalos ..................... 606/170 |
| 5,759,185 A | | 6/1998 | Grinberg |
| 5,843,106 A | | 12/1998 | Heisler |
| 5,863,294 A | | 1/1999 | Alden |
| 5,871,493 A | | 2/1999 | Sjostrom et al. |
| 5,964,777 A | | 10/1999 | Drucker |
| 6,001,116 A | | 12/1999 | Heisler et al. |
| 6,053,928 A | | 4/2000 | Van Wyk et al. |
| 6,068,641 A | | 5/2000 | Varsseveld |
| 6,217,598 B1 | | 4/2001 | Berman et al. |
| 6,309,394 B1 | * | 10/2001 | Staehlin et al. ............... 606/79 |
| 6,440,138 B1 | * | 8/2002 | Reiley et al. .................. 606/79 |
| 2002/0058944 A1 | * | 5/2002 | Michelson .................... 606/79 |

FOREIGN PATENT DOCUMENTS

WO  WO 9208416 A1 *  5/1992

\* cited by examiner

*Primary Examiner*—Thomas C Barrett
*Assistant Examiner*—David W Bates
(74) *Attorney, Agent, or Firm*—Fish & Richardson P.C.

(57) ABSTRACT

A tissue cutting instrument includes an outer member, an inner member received within the outer member, and a cutter coupled to the inner and the outer members such that rotation of the inner member about an axis causes off-axis movement of the cutter. A method of cutting tissue includes positioning an outer member such that the outer member is adjacent tissue, engaging the tissue with a cutter coupled to the outer member, and moving the cutter to end-on cut the tissue. The extended portion of the cutter extends distally beyond a terminal end of the outer member.

8 Claims, 13 Drawing Sheets

TISSUE CUTTING INSTRUMENT

TECHNICAL FIELD

This invention relates to tissue cutting instruments and, more particularly, to cutting blades for cutting tissue at a distal end of a tissue cutting instrument.

BACKGROUND

A conventional tissue cutting blade typically includes two coaxial tubes or members, where one tube rotates or reciprocates within the other. Each tube has geometry cut therein to form the cutting edges. For soft tissue cutting blades, the tubes are matched with minimal clearances to provide a shearing action between them. Bone cutters typically use a burr-type inner member, which does not depend on the outer member for shearing. With both of these designs, the cutting action of the blade is reduced close to the rotational axis of the blade. This is due in part to the surface speed of the blade approaching zero close to the blade axis.

SUMMARY

In one general aspect, a tissue cutting instrument includes an outer member, an inner member received within the outer member, and a cutter coupled to the inner and the outer members such that rotation of the inner member about an axis causes off-axis movement of the cutter.

Some or all of the following features may be included in this aspect of the tissue cutting instrument. The outer member includes a terminal end at a distal end. The terminal end is spherical. Alternatively, the terminal end is flat. The terminal end defines an opening therein and the terminal end opening includes a cutting portion.

The terminal end opening is formed by a cut into the terminal end. Alternatively, the terminal end opening is formed by at least two cuts into the terminal end. Each of the two cuts is cylindrical and the two cuts are perpendicular to each other. Alternatively, each of the two cuts is v-shaped. In another alternative, each of the two cuts is flat.

The outer member includes a first chamber and a second chamber and the chambers are located in an inner surface of the terminal end of the outer member. Each chamber is arch-shaped. The cutter includes a first shaft and a second shaft and each shaft assembles in a respective one of the chambers.

The inner member includes a plurality of teeth at its distal end. The inner member rotates axially and the cutter rotates in a direction perpendicular to the direction of rotation of the inner member.

The cutter is a hollow body and the body defines an opening therethrough. The body is a sphere. The cutter opening includes a cutting portion and an extended portion. The cutter opening is formed by a cut through the cutter. Alternatively, the cutter opening is formed by at least two cuts through the cutter. Each of the two cuts are circular and the two cuts overlap to form a cutting portion and an extended portion. In another alternative, the cutter opening is molded.

The cutter includes a first shaft and a second shaft, and the shafts are located 180° apart from each other along an outer surface of the cutter. The first shaft includes a plurality of teeth extending from an outer circumference of the first shaft. The inner member includes a plurality of teeth on its distal end, and the teeth of the first shaft of the cutter engage with the teeth of the inner member to move the cutter. The inner member rotates axially and the cutter rotates in a direction perpendicular to the direction of rotation of the inner member.

In another general aspect, a method of cutting tissue includes positioning an outer member such that the outer member is adjacent tissue, engaging the tissue with a cutter coupled to the outer member, and moving the cutter to end-on cut the tissue. The extended portion of the cutter extends distally beyond a terminal end of the outer member.

Some or all of the following features may be included in this method for cutting tissue. Engaging the tissue includes slicing into the tissue with the extended portion of the cutter.

Moving the cutter includes rotating an inner member to cause off-axis movement of the cutter. The inner member rotates axially and the cutter rotates in a direction perpendicular to the direction of rotation of the inner member. Alternatively, moving the cutter includes engaging the cutter and an inner member while rotating the inner member.

End-on cutting tissue includes abrading tissue. Alternatively, end-on cutting tissue comprises slicing, grabbing, and shearing tissue.

In another general aspect, a method of cutting tissue includes applying a direct cutting force to tissue with a cutter, and mechanically rotating a member to cause off-axis movement of the cutter to end-on cut tissue.

Some or all of the following features may be included in this method of cutting tissue. End-on cutting tissue includes abrading tissue. Alternatively, end-on cutting tissue includes slicing, grabbing, and shearing tissue.

In another general aspect, a tissue cutting instrument includes an outer member having a terminal end, an inner member received within the outer member, and a cutter coupled to the inner and the outer members. The cutter includes an extended portion extending distal of the terminal end, and the cutter is configured and arranged to perform end-on cutting.

Conventional cutting instruments do not effectively end-on cut tissue when tissue abuts a distal cutting surface of a blade such as when cutting fundal tissue in an intrauterine myomectomy. A typical blade relies on suction to introduce tissue to the cutting surface. Additionally, such blades may rely on shearing of tissue between an inner and an outer member to cut tissue. By changing the axis of rotation of the blade to be different from the axis of rotation of the inner member, e.g., perpendicular to the axis of rotation of the inner member, a tissue cutting instrument can cut more efficiently at its distal end by grabbing and shearing tissue as well as abrading tissue end-on.

The tissue cutting instrument of this invention includes a cutter that rotates off-axis as the inner member rotates axially to end-on cut tissue. In particular, as the cutter rotates off-axis, the cutter slices into targeted tissue, grabs the tissue, and then shears the tissue against the outer member. Internal suction facilitates the removal of debris to reduce the possibility of clogging. The cutter includes a portion that extends distally beyond a terminal end of the outer member to provide for slicing into the tissue, eliminating the need for suction to draw the tissue to the cutting instrument. As a result, the tissue cutting instrument's versatility is enhanced to include cutting soft, semi-hard, and hard tissue. Additionally, the tissue cutting instrument effectively cuts targeted tissue that is presented as a wall perpendicular to the rotation of the inner member such that in use, an operator can hold the tissue cutting instrument with the terminal end of the outer member perpendicular to and directly adjacent to the tissue for end-on cutting.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1A:
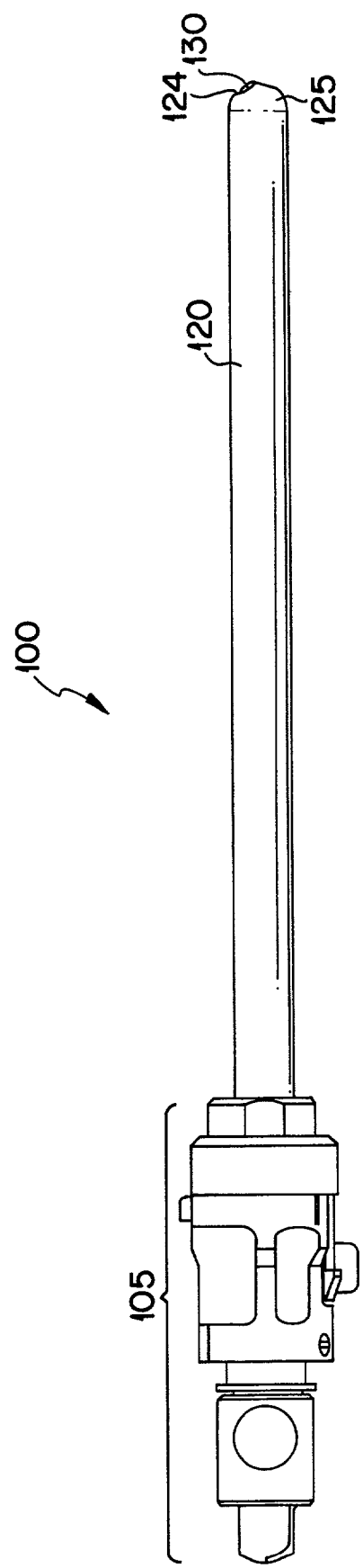
FIG. 1A is a side view of an embodiment of a tissue cutting instrument.
Figure 1B:
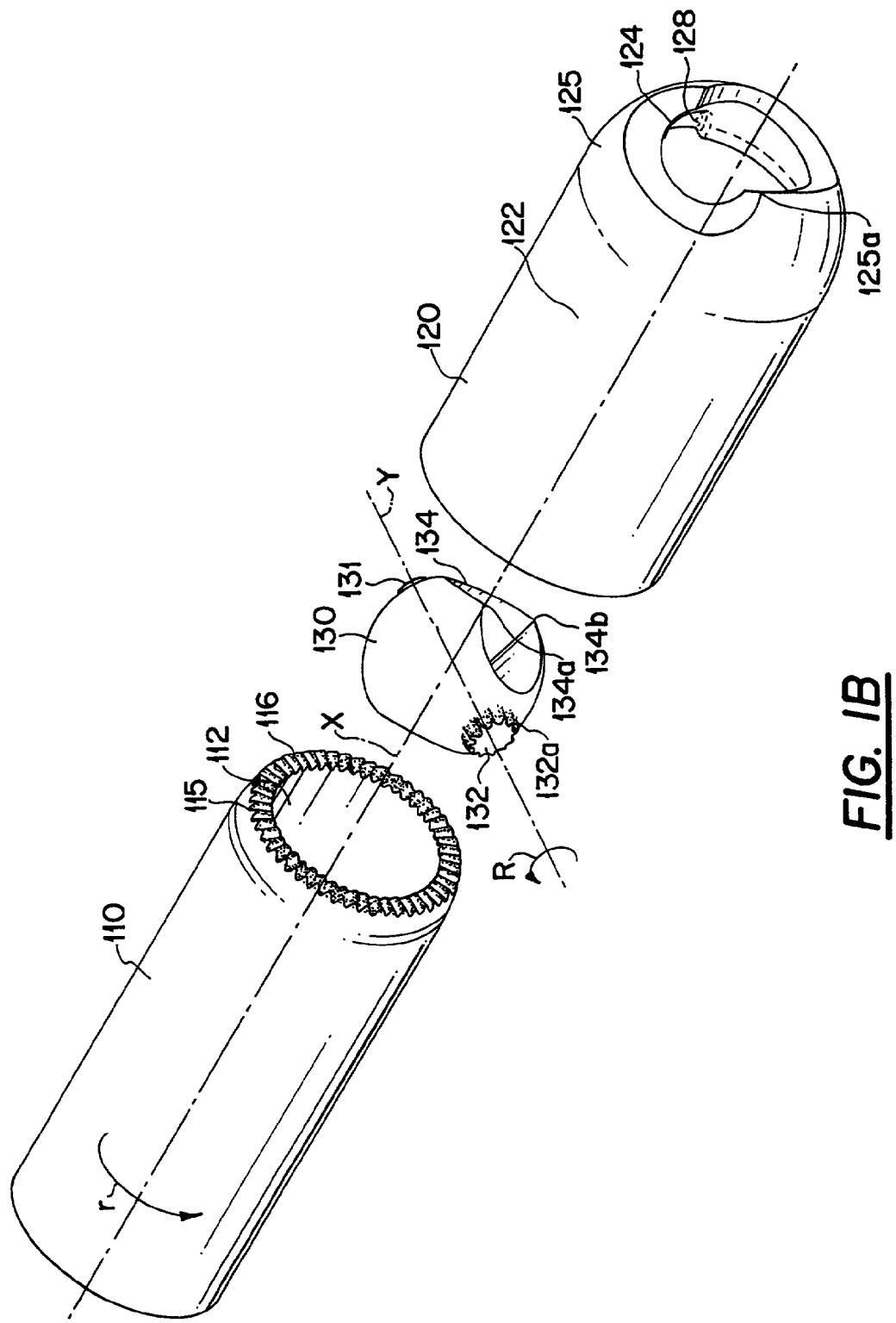
FIG. 1B is an exploded perspective view of a distal portion of the tissue cutting instrument of FIG. 1A.
Figure 2A:
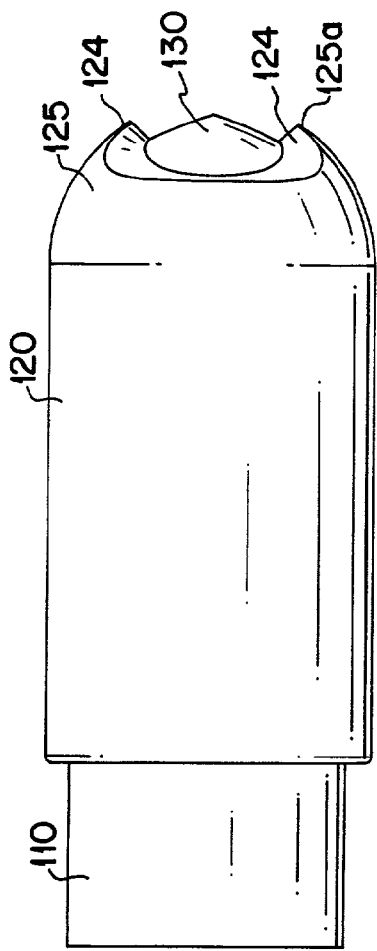
FIG. 2A is a side view of the distal portion of FIG. 1B.
Figure 2B:
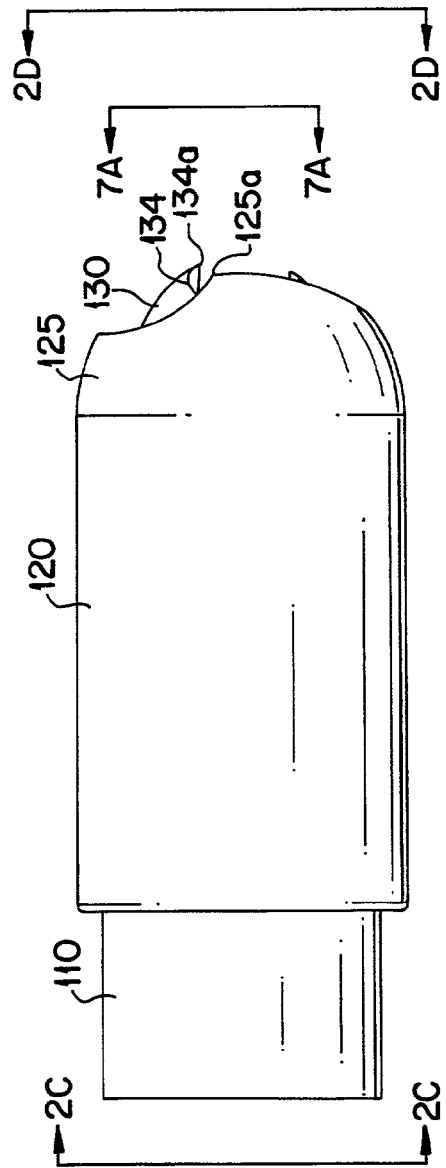
FIG. 2B is another side view of the distal portion of FIG. 2A rotated 90° relative to FIG. 2A.
Figure 2C:
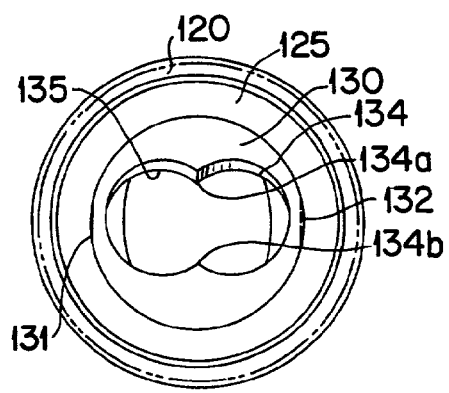
FIG. 2C is an end view of FIG. 2B taken along line 2C-2C in FIG. 2B.
Figure 2D:
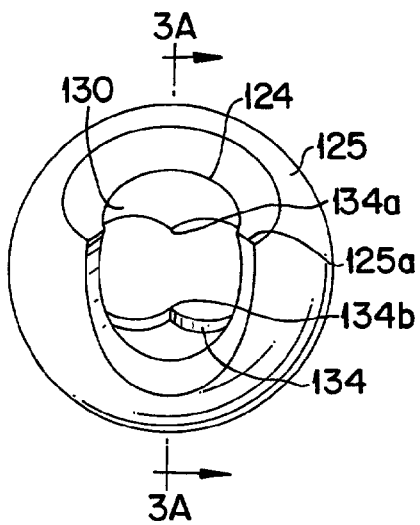
FIG. 2D is an end view of FIG. 2B taken along line 2D-2D in FIG. 2B.
Figure 2E:
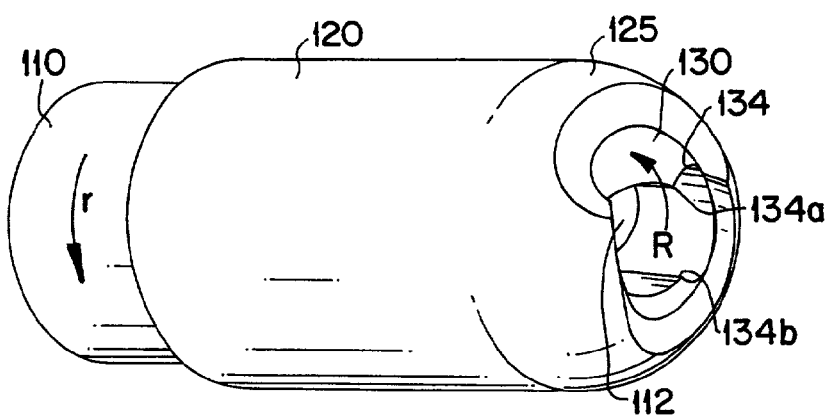
FIG. 2E is a perspective view of the distal portion of FIG. 2B.

Referring to FIGS. 1A and 1B, a tissue cutting instrument 100 for cutting hard, semi-hard, or soft tissue end-on includes a hub 105, an inner member 110, an outer member 120, and a cutter 130. The inner member 110 is received within the outer member 120. The inner 110 and the outer 120 members are coupled together by the hub 105 (as is known for arthroscopic cutting blades having a stationary outer member and an inner member driven by a rotary driver). For instance, U.S. Pat. No. 5,871,493 to Sjostrom et al. assigned to Smith & Nephew describes a motorized handpiece that rotates an inner member. The hub 105 is molded directly to the inner 110 and outer 120 members or, for example, if the hub is metal, then glued, epoxied, or soldered to the inner and outer members, for instance. The cutter 130 is coupled to the inner 110 and the outer 120 members such that rotation of the inner member 110 causes off-axis movement of the cutter 130, as described farther below.

In use, rotation of the inner member 110 about axis X, in the direction shown by r, causes off-axis movement, e.g., rotation, of the cutter 130 about axis Y, in the direction shown by R. As the cutter 130 rotates, the cutter 130 is held directly against the targeted tissue such that the cutter 130 slices into the tissue and then shears the tissue between the cutter 130 and the outer member 120, like the cutting action of a pair of scissors.

Referring to FIGS. 2A-2E, a distal portion of the tissue cutting instrument 100 includes the inner member 110, the outer member 120, and the cutter 130. The cutter 130 includes a cutting edge 134 with a portion 134a that extends distally beyond a terminal end 125a of the distal portion 125 of the outer member 120. As the inner member 110 rotates, as shown by arrow r, the cutter 130 moves off-axis, as shown by arrow R, to slice into tissue. The slice of tissue is then brought into contact with a cutting portion 124 of the outer member 120 where the tissue is sheared off by the motion of the cutting edge 134 of the cutter 130 relative to the cutting portion 124 of the outer member 120. The cut tissue is aspirated away from the surgical site through a hollow interior lumen 112 of the inner member 110.

Figure 3A:
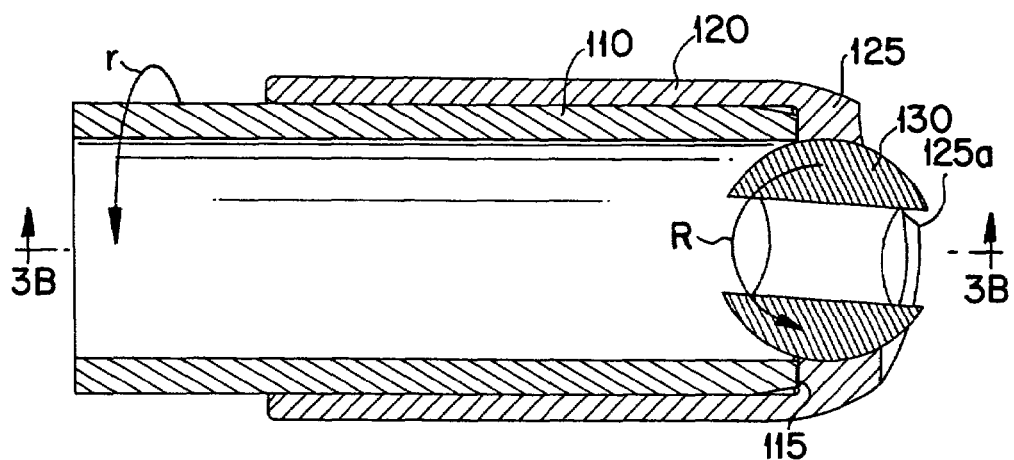
FIG. 3A is a cross-sectional side view of the distal portion of FIG. 2B taken along section 3A-3A of FIG. 2D.
Figure 3B:
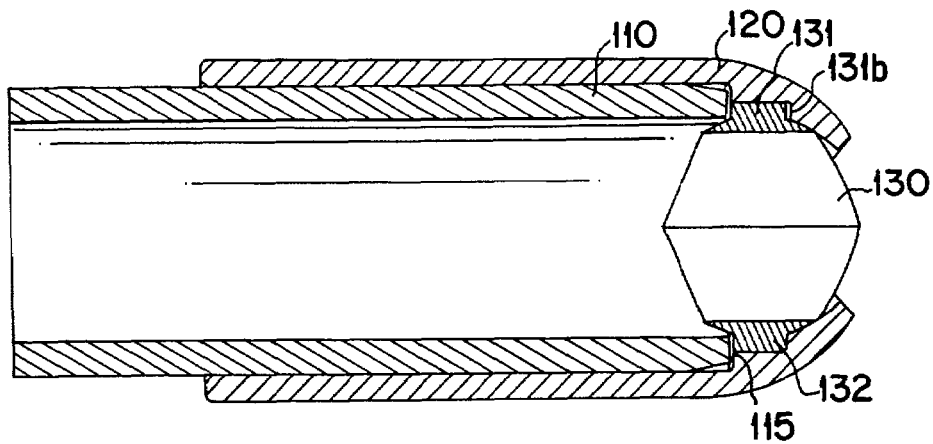
FIG. 3B is a cross-sectional side view of the distal portion of FIG. 2B taken along section 3B-3B of FIG. 3A.

Referring to FIGS. 3A and 3B, cutter 130 is coupled to the inner member 110 and the outer member 120, when the tissue cutting instrument 100 is assembled. Cutter 130 includes shafts 131, 132 located 180° apart on its outer surface. Shaft 132 engages a distal engaging portion 115 of the inner member 110 such that as the inner member 110 is rotated by a rotary driver about axis X, in the direction shown by arrow r, the cutter 130 moves off-axis in the direction shown by arrow R, for example, rotates perpendicular to the rotation of the inner member 110 about axis Y, as described further below.

Referring to FIGS. 4A-4D, the outer member 120 is tubular with a hollow interior 122. The outer member 120 includes a distal portion 125 having cutting portion 124 with a terminal end 125a. The distal portion 125 is, for example, spherical or dome-shaped. This shape of the distal portion 125 assists in retaining or coupling the cutter 130 with the inner 110 and the outer 120 members.

Figure 4A:
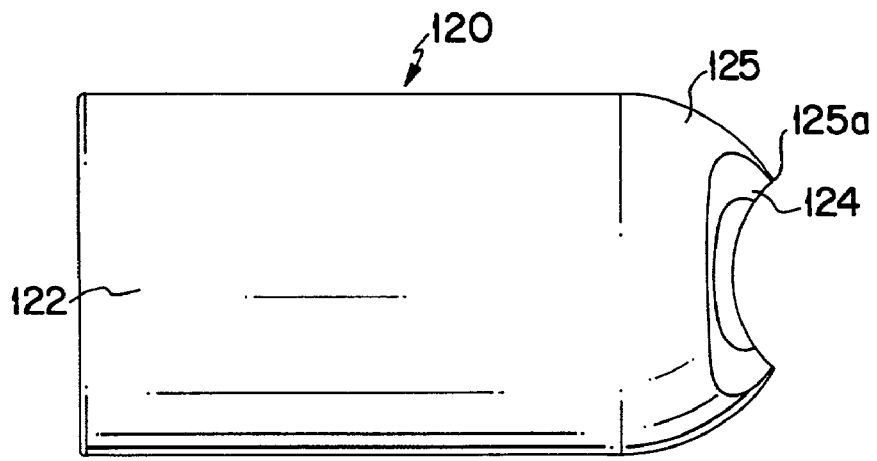
FIG. 4A is a side view of the outer member of the tissue cutting instrument of FIG. 1A.
Figure 4B:
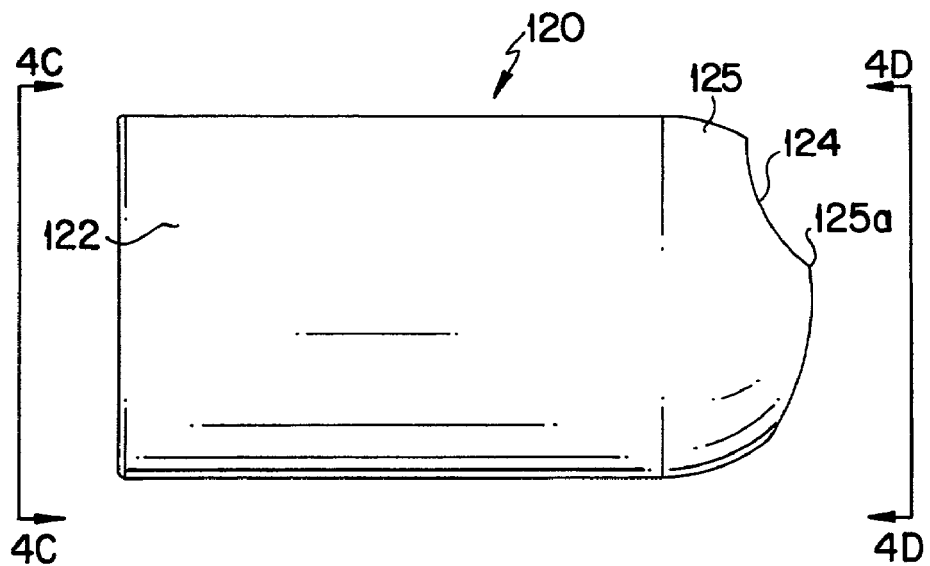
FIG. 4B is another side view of the outer member of the tissue cutting instrument of FIG. 1A, rotated 90° relative to FIG. 4A.
Figure 4C:
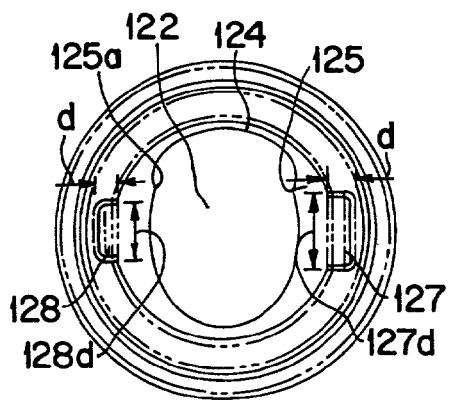
FIG. 4C is an end view of the outer member of FIG. 4B taken along line 4C-4C in FIG. 4B.
Figure 4D:
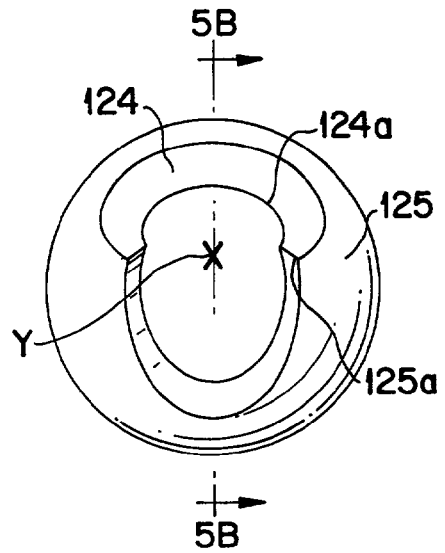
FIG. 4D is an end view of the outer member of FIG. 4B taken along line 4D-4D in FIG. 4B.

The cutting portion 124, as shown in FIG. 4D, for example, is formed by two cylindrical cuts into the distal portion 125 of the outer member 120. The cuts are oriented perpendicular to each other. The edge 124a of the cutting portion 124 is sharpened to provide a sharpened cutting edge against which the tissue is sheared between the cutter 130 and the outer member 120.

Figure 5A:
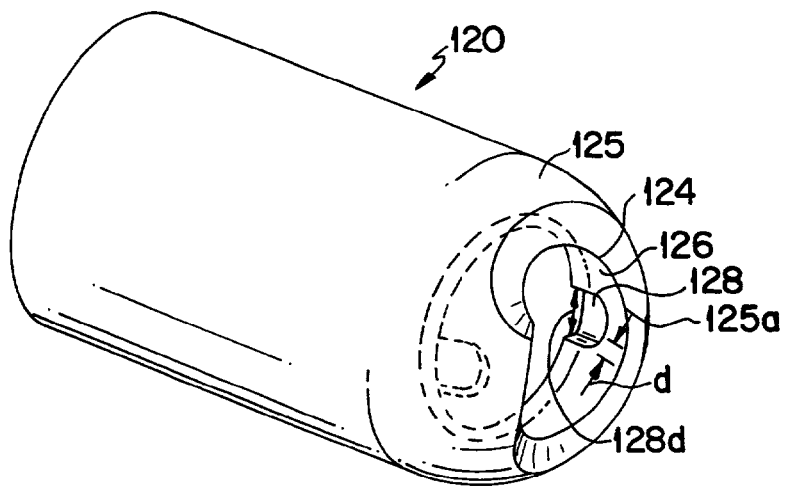
FIG. 5A is a perspective view of the outer member of FIG. 4B.
Figure 5B:
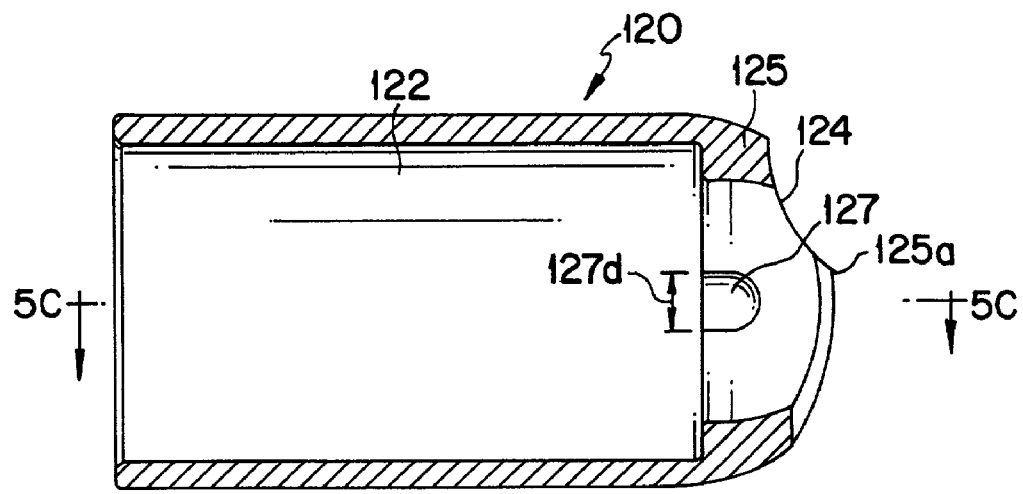
FIG. 5B is a cross-sectional side view of the outer member of FIG. 4B taken along section 5B-5B in FIG. 4D.
Figure 5C:
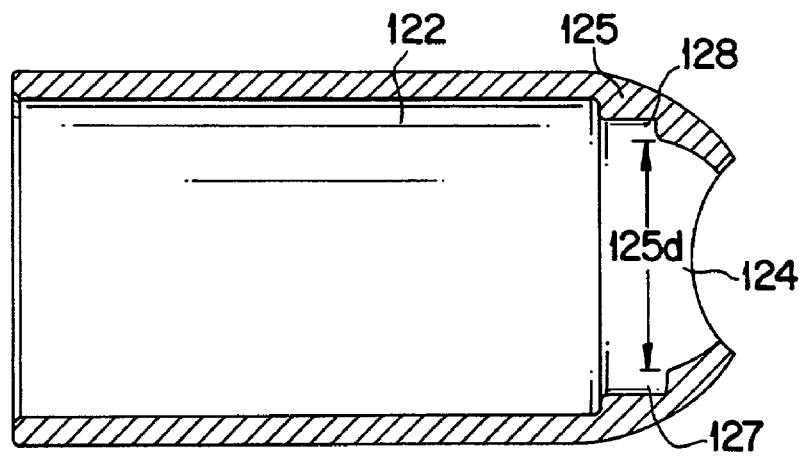
FIG. 5C is a cross-sectional side view of the outer member of FIG. 4B taken along section 5C-5C of FIG. 5B.

Referring to FIGS. 5A-5C, the distal portion 125 of the outer member 120 also includes a spherical shaped interior surface 126, as shown in FIG. 5A. The interior surface 126 includes two chambers 127, 128 for receiving shafts 132, 131, respectively. The chambers 127, 128 are formed in the interior surface 126 and are located 180° apart from each other. Each chamber 127, 128, for example, is arch-shaped with a diameter 127d, 128d and a depth d. Depth d of the chambers 127, 128 provides clearance for a running fit for shafts 131, 132 of the cutter 130. The diameter 127*d* of chamber 127 is larger than the diameter 128*d* of chamber 128. The shafts 131, 132 of the cutter 130 assemble in the chambers 128, 127, respectively, when the cutting instrument 100 is assembled and as described in more detail below.

In addition to providing a shearing surface, the outer member 120 retains the shaft 132 of the cutter 130 against the distal engaging portion 115 of the inner member 110 for purposes described below.

Figure 6A:
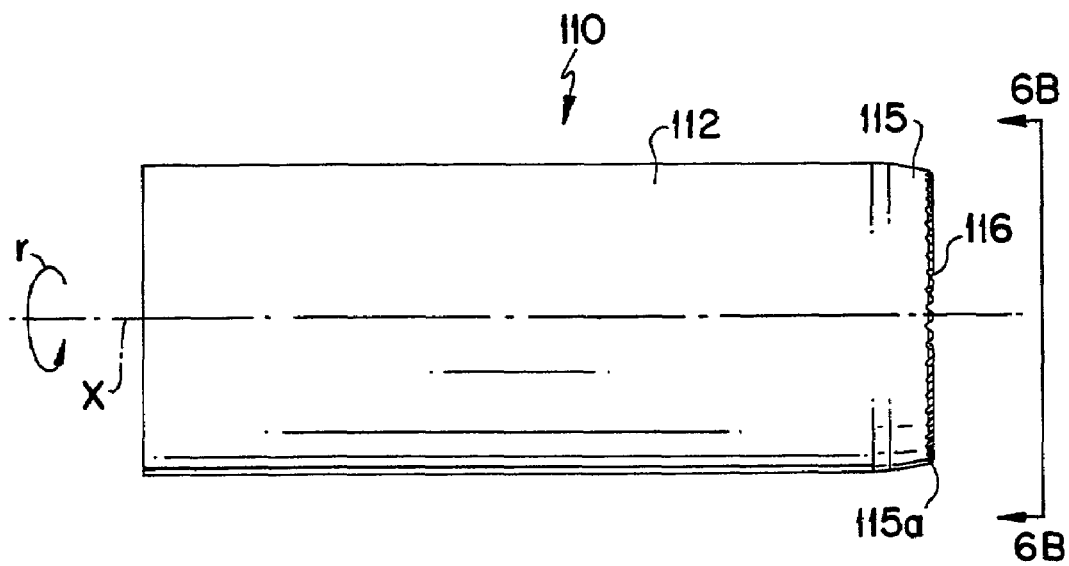
FIG. 6A is a side view of the inner member of the tissue cutting instrument of FIG. 1B.
Figure 6B:
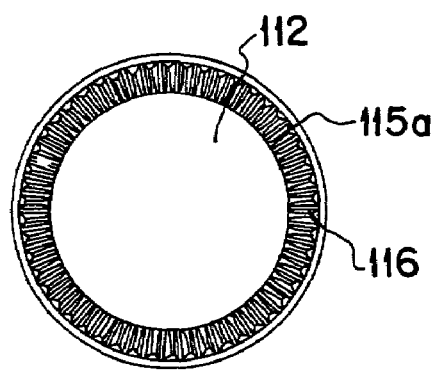
FIG. 6B is an end view of the inner member of FIG. 6A taken along line 6B-6B in FIG. 6A.
Figure 7A:
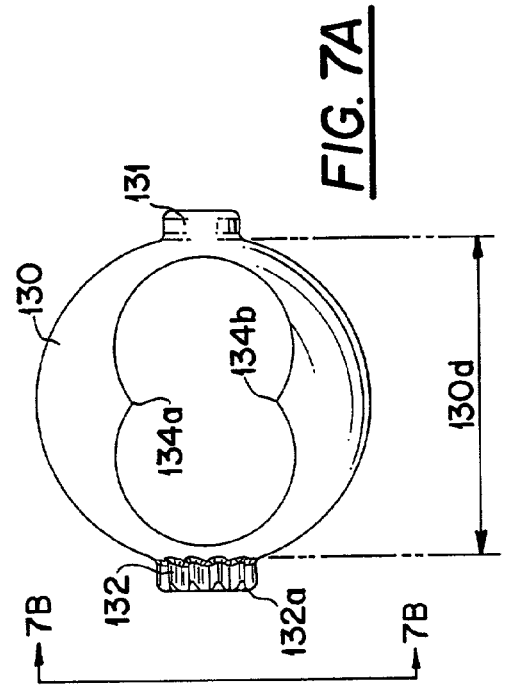
FIG. 7A is an end view of the cutter of the tissue cutting instrument of FIG. 1B taken along line 7A-7A in FIG. 2B.
Figure 7D:
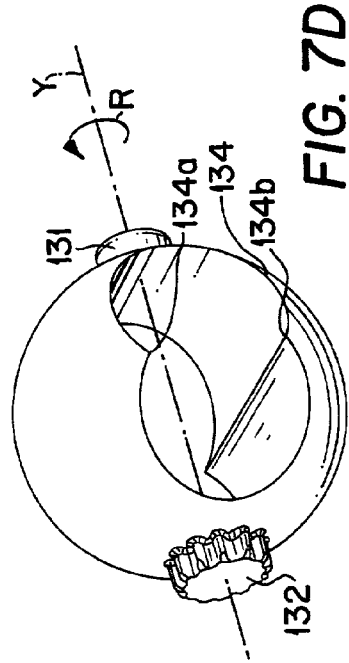
FIG. 7D is a perspective view of the cutter of FIG. 7A.
Figure 7B:
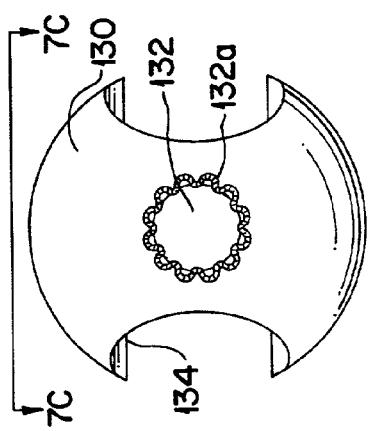
FIG. 7B is a side view of the cutter of FIG. 7A taken along line 7B-7B in FIG. 7A.
Figure 7C:
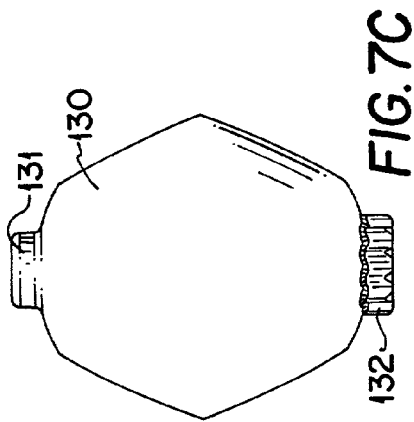
FIG. 7C is an end view of the cutter of FIG. 7A taken along line 7C-7C in FIG. 7B.

Referring to FIGS. 6A and 6B, the inner member 110 is tubular with a hollow interior lumen 112. The inner member 110 includes the distal engaging portion 115 at its distal end. The distal engaging portion 115 includes a plurality of teeth 116 extending from a distal facing circumferential edge 115*a*. A rotary driver, as is known with arthroscopic instruments, rotates inner member 110 about axis X, as shown by arrow r. Hollow interior lumen 112 of the inner member 110 provides a channel through which tissue debris is aspirated away from the surgical site.

Referring to FIGS. 7A-7D, the cutter 130 includes the cutting edge 134 and the shafts 131, 132. The cutting edge 134 of the cutter 130 is formed, for example, by two circular cuts through the cutter 130. The two circular cuts overlap each other to form two extended portions 134*a*, 134*b*, which are each shaped, for example, like a tooth or hook, in the cutting edge 134 that slices into the targeted tissue to initiate a cut. The cutter 130, for example, is a spherical hollow body. Referring particularly to FIG. 5C, the inner diameter 125*d* of the distal portion 125 of the outer member 120 and the outer diameter 130*d* of the cutter 130 are selected to provide a clearance between cutter 130 and outer member 120 for shearing tissue.

The two shafts 131, 132 protrude from the cutter 130 and are located 180° apart from each other on a common diameter, e.g., lie on the axis of rotation of the cutter 130. Shaft 131 has a smooth outer circumference 131*a*. Shaft 132 includes a plurality of teeth 132*a*, protruding from the outer circumference of the shaft 132 such that shaft 132 looks like a gear.

Shafts 131, 132 assemble in chambers 128, 127 of the outer member 120, respectively. The diameter 127*d* of chamber 127 is larger than the diameter 128*d* of chamber 128. The smooth shaft 131 fits in the chamber 128 with diameter 128*d*; the toothed shaft 132 in the chamber 127 with diameter 127*d*. The smooth shaft 131 of the cutter 130 has clearance 131*b* (see FIG. 3B) within chamber 128 such that shaft 131 does not contact the distal engaging portion 115 of the inner member 110.

The teeth 132*a* of shaft 132 of cutter 130 engage with the teeth 116 of the distal engaging portion 115 of the inner member 110. The engagement of the teeth 132*a* of the shaft 132 and the teeth 116 of the distal engaging portion 115 of the inner member 110 translates the rotation of the inner member 110 about axis X (in the direction arrow r) to the off-axis movement of the cutter 130, for example, about axis Y (in the direction of arrow R). As the inner member 110 rotates (as shown by arrow r in FIG. 3A), the cutter 130 moves off-axis, for example, perpendicular to the rotation of the inner member (as shown by arrow R in FIG. 3A).

Figure 8:
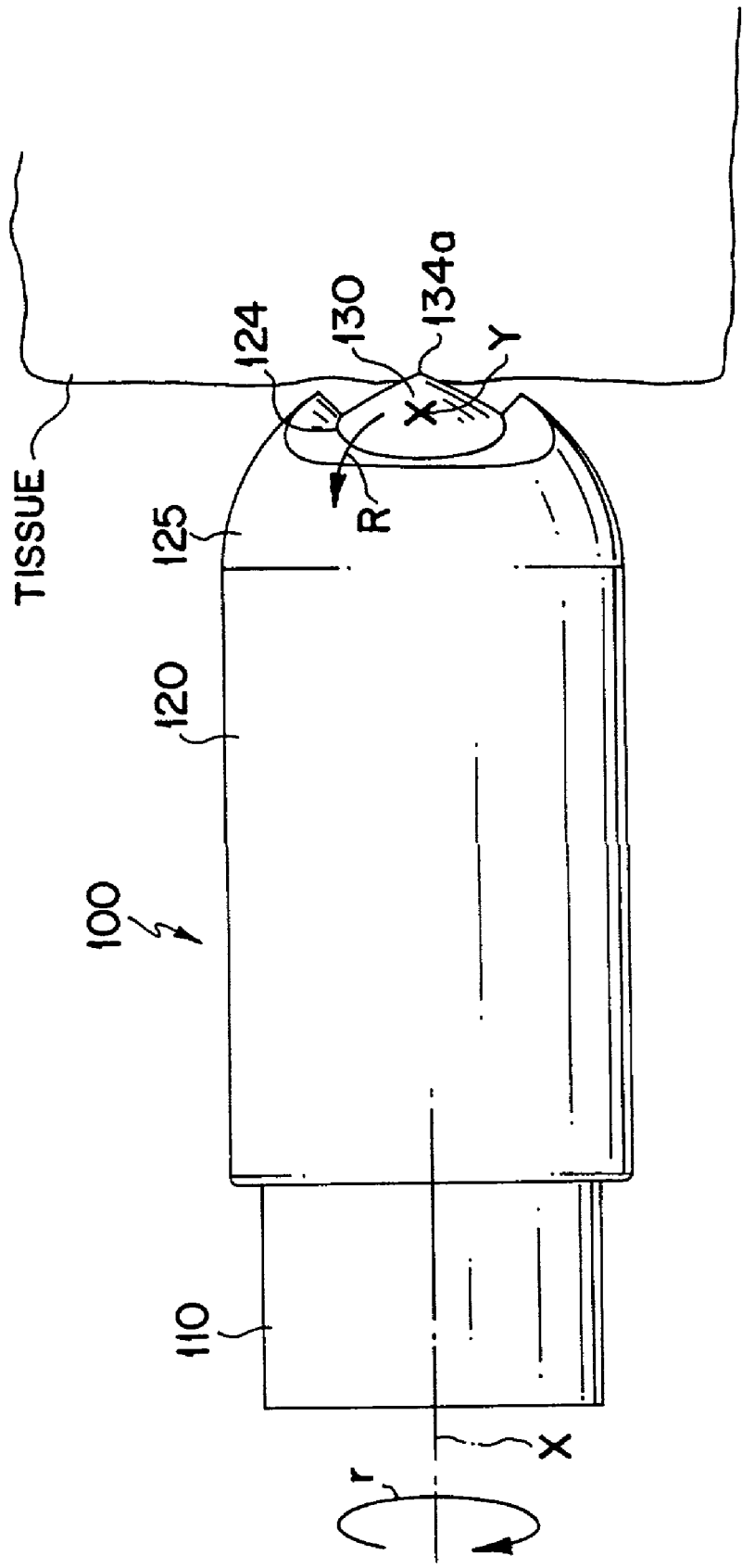
FIG. 8 illustrates the tissue cutting instrument of FIG. 1A in use.

Referring to FIG. 8, in use, an operator holds the distal end of the tissue cutting instrument 100 directly against targeted tissue, for example, fundal tissue in a myomectomy procedure, perpendicular to the tissue for end-on cutting. As the inner member 110 is rotated about axis X (shown by arrow r), the cutter 130 moves off-axis, for example, rotates perpendicular to the rotation of the inner member 110 about axis Y (shown by arrow R), perpendicular to axis X. Extended portion 134*b* of the cutter 130 slices into the targeted tissue, grabbing the tissue. The cutting portions 124, 134 of outer member 120 and cutter 130, respectively, shear the tissue and the cut tissue is aspirated away along hollow interior 112 of the inner member 110. Additionally, where the tissue is particularly hard and the cutter 130 is unable to slice into the targeted tissue, the cutter 130 abrades the targeted tissue as it rotates, and the debris is aspirated away along the hollow interior lumen 112 of the inner member 110.

Figure 9A:
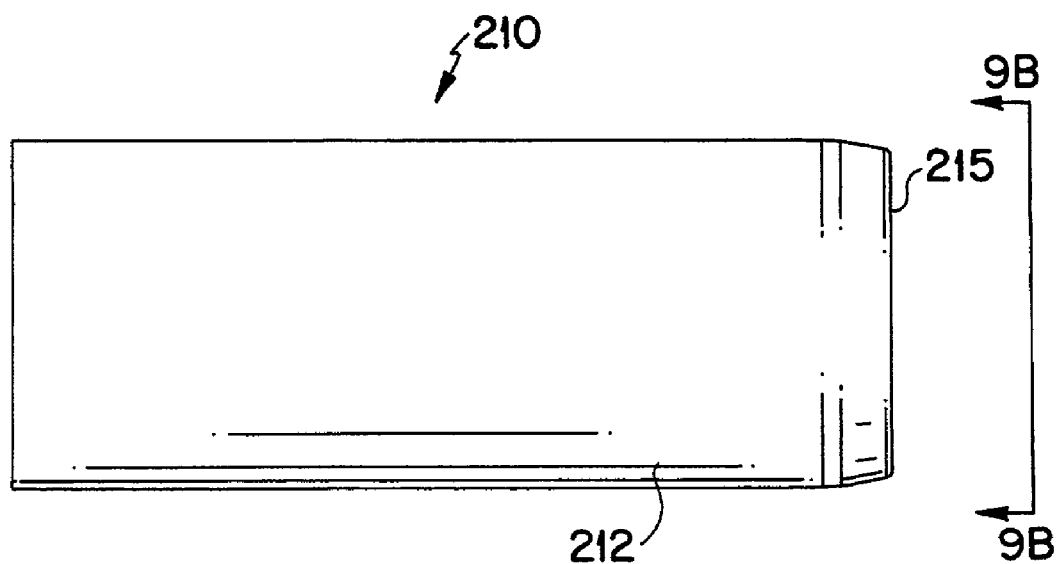
FIG. 9A is a side view and FIG. 9B is an end view of an alternative embodiment of the inner member of the tissue cutting instrument.
Figure 9B:
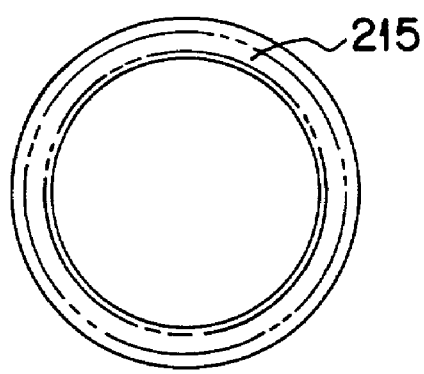
Figure 10A:
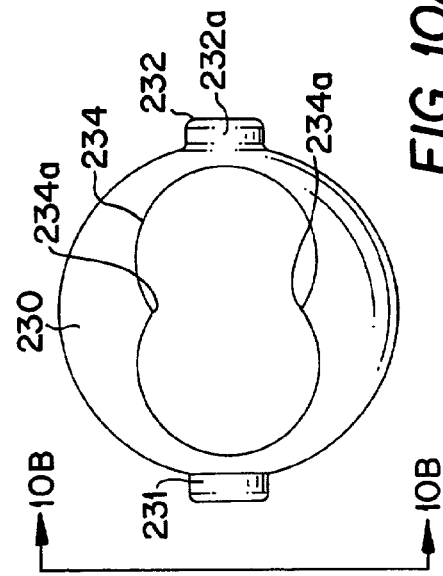
FIG. 10A is an end view of an alternative embodiment of the cutter of the tissue cutting instrument.
Figure 10B:
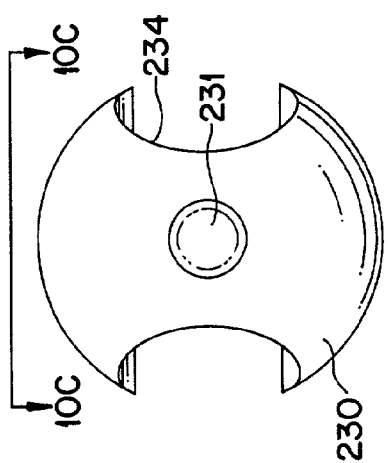
FIG. 10B is a side view of the cutter of FIG. 10A taken along line 10B-10B in FIG. 10A.
Figure 10C:
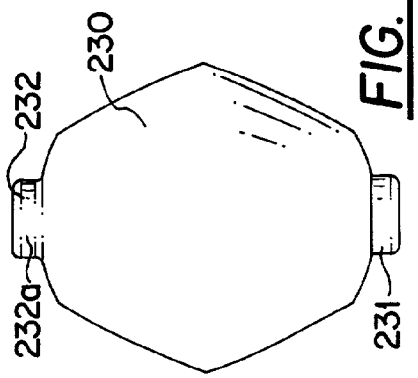
FIG. 10C is an end view of the cutter of FIG. 10A taken along line 10C-10C in FIG. 10B.
Figure 10D:
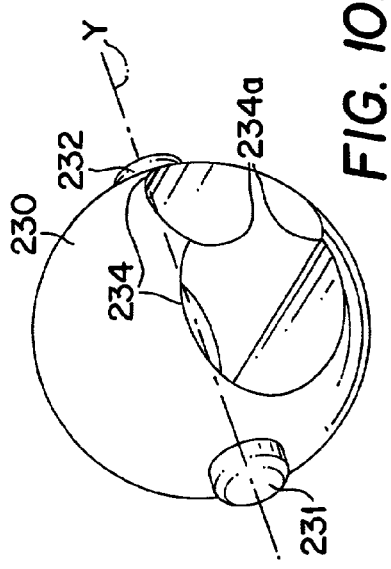
FIG. 10D is a perspective view of the cutter of FIG. 10A.

Other embodiments are within the scope of the following claims. For example, referring to FIGS. 9A and 9B, the distal engaging portion 215 of the inner member 210 is smooth. Referring to FIGS. 10A-10D, the cutter 230 includes two smooth shafts 231, 232. As above, the two shafts 231, 232 fit within the chambers 128, 127 of the outer member 120. Similar running fits and clearances as described above apply. Shafts 232 has a rubber surface 232*a*, for example, an O-ring, provided thereon. The O-ring 232*a* provides a source of friction against the distal engaging portion 215 of the inner member 210. This frictional force causes the cutter 230 to rotate off-axis to end-on cut tissue, as described above. As the inner member 210 is rotated, the cutter 230 moves off-axis, for example, rotates perpendicular to the rotation of the inner member 210, as a result of the friction between the shaft 232 with the rubber surface 232*a* moving against the smooth distal engaging portion 215 of the inner member 210.

Shaft 231 of the cutter 230 (without a rubber surface) has clearance (like 131*b* above) within the chamber 127 of the outer member 120 from the inner member 210 so that cutter 230 moves when smooth distal engaging portion 215 contacts rubber surface 232*a*.

Dimensions of the members vary with the specific application or use of the cutting instrument. Dimensional tolerances, such as, for example, clearance between the inner and outer members, are similar to those as known with conventional arthroscopic cutting blades.

A number of embodiments have been described. Nevertheless, it will be understood that various modifications may be made without departing from the spirit and scope. For example, the instrument includes lubrication for its parts or a coating on the cutter. Alternatively, a spacer or a washer is added to the chambers or smooth shaft to reduce friction thus reducing any tendency of the cutter to move on-axis with the inner member. The cutter can have a cylindrical shape. The distal portion of the outer member can be cylindrical or conical. The terminal end of the outer member can be flat or angled. As an alternative, the cutting portion can be formed by flat cuts or v-shaped grooves or other combinations of shapes. The circular cuts in the cutter, in another alternative, are, for example, two overlapping diamond shaped cuts or three diamonds or circles providing two extended portions. Alternatively, the cutting portion of the cutter can have a single extended portion on one side and two extended portions on another side or other configurations that vary with the specific application or use. The inner member rotates, in one alternative, in either direction or reciprocates back and forth about axis X such as in a soft tissue procedure. Alternatively, in use, the cutting instrument can be held at a range of angles in relation to the targeted tissue from just greater than 0° to just less than 180°. Accordingly, other embodiments are within the scope of the following claims.

What is claimed is:

1. A tissue cutting instrument, comprising:
   an outer member;
   an inner member received within the outer member; and
   a cutter coupled to the inner and the outer members such that rotation of the inner member about an axis causes off-axis movement of the cutter, the cutter including a lumen having two open ends, the lumen having an axis extending between the two open ends of the lumen, wherein the cutter comprises first and second protruding shafts having centers located 180° apart from each other along an outer surface of the cutter, the shafts being aligned transverse to the lumen axis, and wherein the first shaft comprises a plurality of teeth extending from an outer circumference of the first shaft.

2. The instrument of claim 1 wherein the inner member includes a plurality of teeth on its distal end, and the teeth of the first shaft of the cutter engage with the teeth of the inner member to move the cutter.

3. The instrument of claim 2 wherein the inner member rotates axially and the cutter rotates in a direction perpendicular to the direction of rotation of the inner member.

4. The instrument of claim 1 wherein the cutter is configured to cut tissue by shearing the tissue between a surface of the cutter and another surface of the tissue cutting instrument and wherein the shearing of the tissue occurs against the surface of the cutter and against the other surface of the tissue-cutting instrument.

5. The instrument of claim 1, wherein a maximum tangential speed of the cutter is at a center of cutting action.

6. A tissue cutting instrument, comprising:
an outer member;
an inner member received within the outer member; and
a generally spherical cutter coupled to the inner and the outer members such that rotation of the inner member about an axis causes off-axis movement of the cutter, wherein the cutter comprises a first shaft and a second shaft, the first shaft protruding from a first surface portion of the cutter and the second shaft protruding from a second surface portion of the cutter, the first surface portion and the second surface portion being opposing surface portions such that centers of the first and second shafts are located 180° apart from each other along an outer surface of the cutter, and wherein the first shaft comprises a plurality of teeth extending from an outer circumference of the first shaft.

7. The instrument of claim 6, wherein the cutter defines a through bore having an axis extending between open ends of the through bore and the first shaft and the second shaft are aligned transverse to the through bore axis.

8. The instrument of claim 6 wherein the cutter is configured to cut tissue by shearing the tissue between a surface of the cutter and another surface of the tissue cutting instrument and wherein the shearing of the tissue occurs against the surface of the cutter and against the surface of the outer member.

* * * * *

UNITED STATES PATENT AND TRADEMARK OFFICE
CERTIFICATE OF CORRECTION

PATENT NO. : 7,641,667 B2  Page 1 of 1
APPLICATION NO. : 10/058122
DATED : January 5, 2010
INVENTOR(S) : Philip B. Sample It is certified that error appears in the above-identified patent and that said Letters Patent is hereby corrected as shown below:

Column 4, line 12, delete "farther" and insert -- further --.

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO.       : 7,641,667 B2
APPLICATION NO.  : 10/058122
DATED            : January 5, 2010
INVENTOR(S)      : Philip B. Sample It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1089 days.

Signed and Sealed this

Twenty-first Day of December, 2010

David J. Kappos
*Director of the United States Patent and Trademark Office*